(12) United States Patent
Hur et al.

(10) Patent No.: US 6,677,748 B2
(45) Date of Patent: Jan. 13, 2004

(54) METHOD OF DISCRIMINATING THROUGH-WALL CRACKS AND MEASURING THROUGH-WALL LENGTH OF CRACKS IN NUCLEAR STEAM GENERATOR TUBES USING EDDY CURRENT SIGNALS

(75) Inventors: Do-Haeng Hur, Daejeon-Si (KR); Myung-Sik Choi, Daejeon-Si (KR); Deok-Hyun Lee, Seoul (KR); Jung-Ho Han, Daejeon-Si (KR)

(73) Assignee: Korea Atomic Energy Research Institute, Daejeon (KR)

( * ) Notice: Subject to any disclaimer, the term of this patent is extended or adjusted under 35 U.S.C. 154(b) by 0 days.

(21) Appl. No.: 10/125,466

(22) Filed: Apr. 19, 2002

(65) Prior Publication Data

US 2002/0153883 A1 Oct. 24, 2002

(30) Foreign Application Priority Data

Apr. 23, 2001 (KR) ........................................ 2001-21684

(51) Int. Cl.[7] ............................................... G01N 27/90
(52) U.S. Cl. ...................... 324/220; 324/240; 165/11.2
(58) Field of Search .................................... 324/219, 220, 324/221, 233, 240, 241, 242; 165/11.1, 11.2; 376/249

(56) References Cited

U.S. PATENT DOCUMENTS

| 3,593,122 | A | * | 7/1971  | Barton et al. .............. 324/220 |
| 4,628,260 | A | * | 12/1986 | Kimoto et al. ............. 324/220 |
| 5,748,003 | A | * | 5/1998  | Zoughi et al. ............. 324/644 |
| 5,821,747 | A | * | 10/1998 | Atherton et al. ........... 324/220 |
| 6,127,823 | A | * | 10/2000 | Atherton .................... 324/220 |
| 6,519,535 | B1 | * | 2/2003 | Petri et al. ................... 702/42 |

* cited by examiner

*Primary Examiner*—Jay Patidar

(57) ABSTRACT

Disclosed herein is a method of discriminating a through-wall crack and measuring the through-wall length of the crack in a steam generator tube of a nuclear power plant. The method of the present invention is characterized in that the through-wall crack is discriminated and the through-wall length of the crack is measured in such a way that there are measured the number and positions of inflection points of a graph that is plotted by relating characteristic amplitude values of eddy current signals, which are generated whenever a coil of a motorized rotating probe passes the crack while being spirally rotated, to the positions in the length of the crack.

5 Claims, 2 Drawing Sheets

METHOD OF DISCRIMINATING THROUGH-WALL CRACKS AND MEASURING THROUGH-WALL LENGTH OF CRACKS IN NUCLEAR STEAM GENERATOR TUBES USING EDDY CURRENT SIGNALS

BACKGROUND OF THE INVENTION

1. Field of the Invention

The present invention relates to a method of discriminating a through-wall crack and measuring the through-wall length of the crack formed in a steam generator tube of a nuclear power plant.

2. Description of the Prior Art

In general, steam generator tubes of a nuclear power plant often undergo various kinds of corrosion and mechanical damage under the operation condition, such as stress corrosion cracking, pitting, inter-granular attack, wear, etc. Such corrosion and degradation are principal factors that affect the safety and integrity of major components of nuclear power plants.

In particular, the occurrence of through-wall cracking of a steam generator tube may result in the serious contamination of a system and environment due to the leakage of primary coolant, including the radioactive contamination of a secondary side. Therefore, it is very important to develop an advanced technique to discriminate the evolution of through-wall cracking in an early stage and to measure its size and length accurately.

The formation and growth of all kinds of defects in a steam generator tube are usually inspected and evaluated by a nondestructive test during a periodic in-service inspection that is normally carried out after each operation cycle.

For a steam generator tube inspection, an eddy current test is usually employed in order to detect and measure various kinds of defects. Generally, a bobbin coil probe and a motorized rotating probe are mainly used.

For volumetric defects formed in a steam generator tube, their sizes can be basically assessed in terms of percentage of defect depth to tube wall thickness taking into account of phase angle in eddy current signal characteristic related to these kinds of defects. However, this evaluation has a very low confidence level.

For crack defects, on the other hand, the detection of cracks themselves and the quantitative evaluation of crack sizes using eddy current test are difficult in comparison with volumetric defects.

Since these technical difficulties, a testing method for detecting a crack, a quantitative evaluation method for determining crack size, and a proper measure criterion for a defected tube are not clearly prescribed even in eddy current testing standards such as the American Society of Mechanical Engineers (ASME) codes.

Furthermore, it is almost impossible to determine whether a crack completely penetrates the wall thickness of a steam generator tube and to measure the through-wall length of the crack.

Currently, in nuclear power plants, the presence of a through-wall crack of a steam generator tube is determined by an in-situ pressure test that is an indirect way to assess a cracking condition of a suspected tube by observation on a leakage of coolant through a crack or a pressure change of coolant.

This mechanical test method is disadvantageous in that a widening and permanent deformation of the crack may arise from an intentional pressurization to a primary or secondary side, the measurement of a through-wall crack length is not possible, the test results are not reliable, an additional testing time and costs are consumed and large-sized equipments are required.

Therefore, it is required to develop a method that can discriminate the through-wall crack and measure accurately through-wall length of the crack using the eddy current signals collected from periodic inspections.

SUMMARY OF THE INVENTION

The present invention relates to an eddy current test method which can discriminate the through-wall crack formed in a steam generator tube and measure accurately its through-wall length using a motorized rotating probe.

In more detail, the present invention is characterized in that a through-wall crack is discriminated and the through-wall length of the crack is measured by relating the characteristic amplitude values of eddy current signals, which are generated whenever a pancake coil, or a combination of a pancake coil and one of a plus point coil, an axial coil and a circumferential coil circumferentially provided on the surface of a motorized rotating probe passes the crack while being spirally rotated, to the positions in the length of the crack.

Accordingly, the present invention has been made keeping in mind the above problems occurring in the prior art, and an object of the present invention is to provide an unique nondestructive method, which is capable of precisely determining whether a crack formed in a steam generator tube of nuclear power plant is a through-wall or non-through-wall crack and precisely measuring the through-wall length of the crack using an amplitude curve of the eddy current signals of a motorized rotating probe.

In order to accomplish the above object, the present invention provides a method of discriminating the through-wall crack and measuring the through-wall length of the crack in the steam generator tube of a nuclear power plant, characterized in that the through-wall crack is discriminated and the through-wall length of the crack is measured in such a way that the number and positions of inflection points are measured on a graph that is plotted by relating the characteristic amplitude values of eddy current signals to the corresponding positions in the length of the crack, which are generated whenever a coil of a motorized rotating probe passes the crack while rotating spirally, moving along the length of the crack.

Preferably, the coil of the motorized rotating probe should be composed of a pancake coil, or a combination of a pancake coil and one of a plus point coil, an axial coil and a circumferential coil.

The method may be carried out using a computer program.

BRIEF DESCRIPTION OF THE DRAWINGS

The objects, features and other advantages of the present invention will be more clearly understood from the following detailed description taken in conjunction with the accompanying drawings, in which.

DESCRIPTION OF THE PREFERRED EMBODIMENTS

A motorized rotating probe inserted into the inside of a steam generator tube is moved along the length of the tube at a constant speed while being rotated at a constant revolution rate. The coil of the motorized rotating probe is composed of a pancake coil, or a combination of a pancake coil and one of a plus point coil, an axial coil and a circumferential coil.

The motorized rotating probe and its structure are conventional, and so the detailed illustration and description of them are omitted When a crack is present in a steam generator tube, an eddy current signal is induced in the coil of the motorized rotating probe, and is converted to digital data and stored by means of a computer. Since the probe is rotated, an eddy current signal can be obtained whenever the coil passes the crack. The motorized rotating probe is moved along the length of the steam generator tube while being rotated, so the through-wall crack in the tube can be precisely discriminated and the through-wall length of the crack can be precisely measured in a graph that is drawn up by relating the characteristic amplitude values of eddy current signals to the positions in the length of the crack. That is, for a through-wall crack, the curve of the characteristic amplitude values related to the positions in the length of the crack has three inflection points, and the length between two maximum points becomes the through-wall length of the crack.

The present invention is described with reference to a preferred embodiment and the accompanying drawings.

Figure 1:
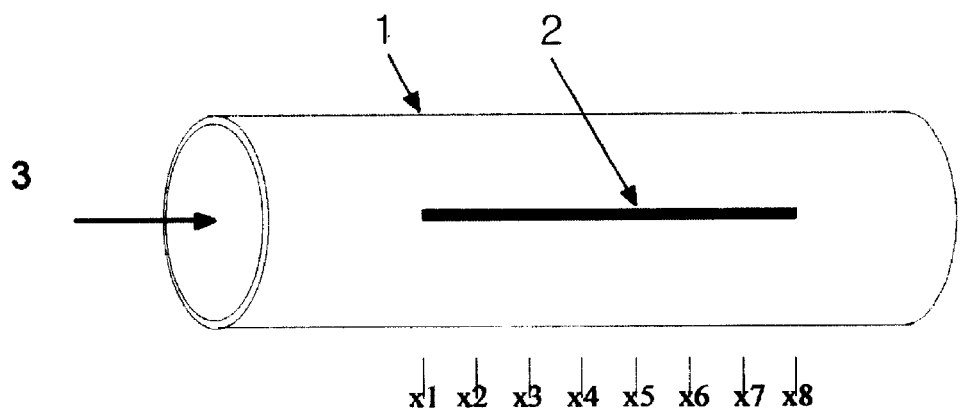
FIG. 1 is a view showing a process in which a steam generator tube undergoes an eddy current test by means of a motorized rotating probe, eddy current signals are obtained and the characteristic amplitude values of the eddy current signals are related to position in the length of the crack.

FIG. 1 is a view showing a process in which a steam generator tube undergoes an eddy current test by means of a motorized rotating probe, eddy current signals are obtained and the characteristic amplitude values of the eddy current signals are related to the positions in the length of a crack. There is an axial crack 2 in a steam generator tube 1. The motorized rotating probe, as illustrated in FIG. 1, is inserted into the steam generator tube 1, and is moved along the length of the tube 3 at a certain speed while being rotated at a certain revolution rate. As the coil of the motorized rotating probe approaches the crack 2, an eddy current signal is gradually induced. Positions where the coil meets the crack 2 are x1, x2, x3, ..., x8. As the coil moves away from the positions, the eddy current signal gradually fades away. A graph of characteristic amplitude values with respect to the positions in the length of the crack 2 is drawn up by plotting positions where eddy current signals are obtained, that is, the positions in the length of the crack 2, over an x-axis, and by plotting the characteristic amplitude values of the eddy current signals obtained at corresponding positions over an y-axis (see FIGS. 2 and 3).

Figure 2:
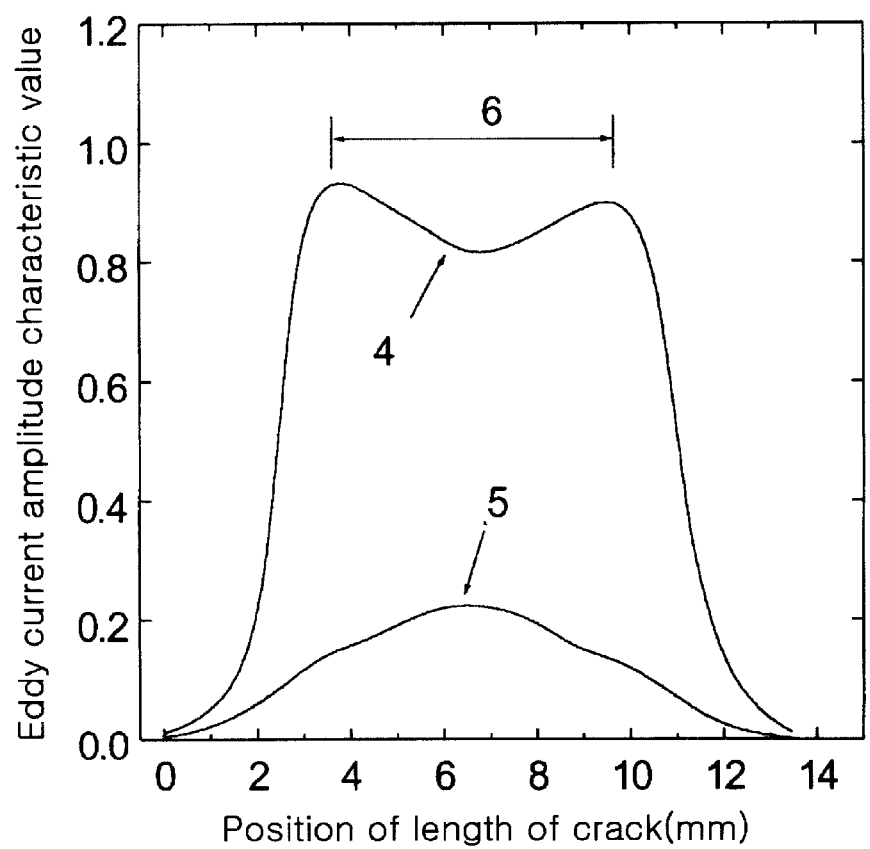
FIG. 2 is a graph showing a method in which the axial through-wall crack of a steam generator tube is discriminated and the through-wall length of the crack is measured using the characteristic amplitude values of the eddy current signal from a pancake coil.

In FIG. 2, it can be determined whether the axial crack 2 completely penetrates the tube wall thickness or not, and also the through-wall length of the crack 2 can be measured. The length of the axial crack machined by known methods such as electric charging to be 6.0 mm for both through-wall and non-through-wall axial cracks (see reference numerals 4 and 5, respectively). The eddy current test is carried out on these cracks using a motorized rotating probe equipped with a pancake coil. For the through-wall crack, when the characteristic amplitude values of eddy current signals, which are obtained whenever the coil passes the crack, are related to positions in the length of the crack, three inflection points (or two peaks in the amplitude) appear. In this case, the position of the maximum amplitude value is the location of through-wall to non-through-wall transition, so the through-wall length 6 of the crack can be accurately obtained by measuring the distance between two maximum positions. The length 6 measured in such a manner is 5.9 mm, and substantially coincides with 6.0 mm that is measured in a direct measuring manner. The non-through-wall crack has a single inflection point (or a single peak in the amplitude), so the through-wall and non-through-wall cracks can be clearly distinguished from each other. The above-described embodiment utilizes characteristic amplitude values obtained from the pancake coil, but similar results are obtained even though characteristic amplitude values obtained from a plus point coil, an axial coil or a circumferential coil are utilized.

Figure 3:
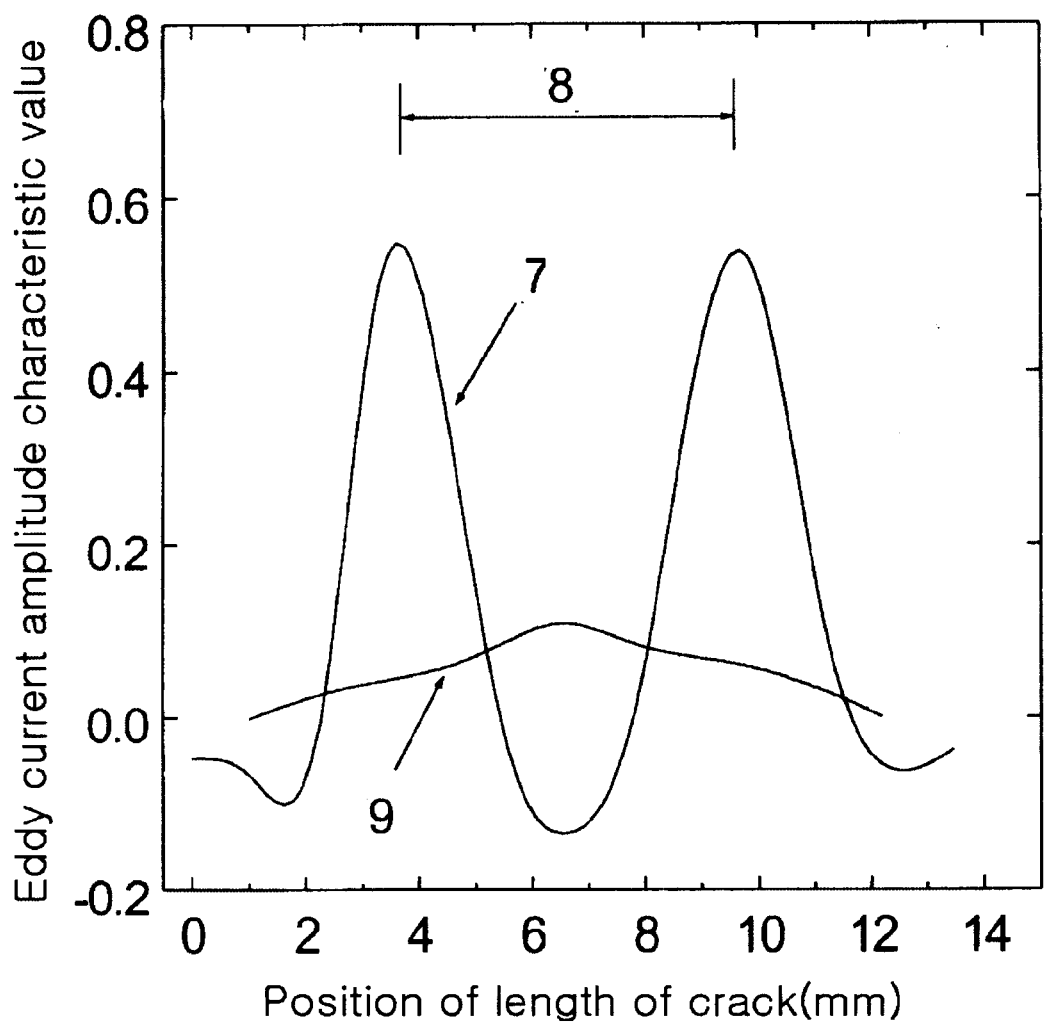
FIG. 3 is a graph showing a method in which the axial through-wall crack of a steam generator tube is discriminated and the through-wall length of the crack is measured using differences between the characteristic amplitude values of eddy current signals from a pancake coil and a plus point coil.

In addition, when the difference values in the characteristic amplitude values between the pancake coil and another coil are related to the positions in the length of a crack, the same results are obtained. FIG. 3 is a graph in which the difference values in the characteristic amplitude values between the pancake coil and another coil, which are obtained while eddy current tests are carried out for the through-wall and non-through-wall cracks employed for FIG. 2 by using a motorized rotating probe equipped with pancake and plus point coil, are related to the positions in the length of the crack 2. For the through-wall crack (see reference numeral 7), there appear three inflection points (or two peaks in the amplitude), which are much more obvious in comparison with FIG. 2. The through-wall length 8 of the crack can be obtained by measuring a length between two maximum points (or by measuring the distance between two peak points in the amplitude). The length 8 measured in such a manner is 5.9 mm, and substantially coincides with 6.0 mm that is measured in a direct measuring manner. The non-through-wall crack (see reference numeral 9) has a single inflection point (or a single peak in the amplitude), so it shows a characteristic considerably different from the through-wall crack, thereby precisely determining whether or not a crack completely penetrates the tube wall thickness.

The number of eddy current amplitude signals, which are obtained with regard to a crack of a certain length, varies according to a rotating speed of the probe and a drawing speed at which the probe is moved in the longitudinal direction of the steam generator tube. Accordingly, if the rotating speed of the probe is increased or its drawing speed is decreased, the number of amplitude signals obtained for each unit length is increased, and thus gives more precise results.

In order to obtain precise results, it is necessary to carry out an eddy current signal correction prior to the eddy current test. The eddy current signal correction is carried out using a standard calibration specimen in which through-wall cracks of different lengths are axially and circumferentially formed and non through-wall cracks of different depths are formed on a tube having the same material and specifications as a steam generator tube to be tested.

A computer program can be employed to discriminate the through-wall crack and to measure the through-wall length of the crack in the steam generator tube by using the characteristic amplitude values of eddy current signals that are generated whenever the coil of the motorized rotating probe passes the crack while being spirally rotated.

The above-described embodiment is only an example. All discriminating and measuring methods, which includes a concept in which the through-wall crack is discriminated and the through-wall length of the crack is measured by relating the characteristic amplitude values of eddy current signals, which are generated whenever the coil of the motorized rotating probe passes the crack while being spirally rotated, to the position in the length of the crack, fall under the scope of the present invention.

When the method of the present invention is applied to nondestructive test for steam generator tubes of nuclear power plants, it can be precisely determined whether a crack penetrates the entire wall thickness of the am generator tube and the through-wall length of the crack can be precisely measured. Accordingly, the integrity of the am generator tubes is precisely predicted and evaluated, the damaged tubes can be opportunely repaired, and the coolant leakage from the primary side to the secondary side can be prevented. Especially, in some countries, no leakage of the primary side coolant is permitted, so it is important to determine previously whether a crack will completely penetrate the wall thickness of the steam generator tube. The method of the present invention can be used to fulfill such a requirement.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of discriminating a through-wall crack and measuring a through-wall length of the crack in a steam generator tube of a nuclear power plant, characterized in that:

the through-wall crack is discriminated and the through-wall length of the crack is measured in such a way that there are measured the number and positions of inflection points of a graph that is plotted by relating characteristic amplitude values of eddy current signals, which are generated whenever a coil of a motorized rotating probe passes the crack while being spirally rotated, to position in a length of the crack.

2. The method according to claim 1, wherein the coil of the motorized rotating probe is composed of a pancake coil, or a combination of a pancake coil and one of a plus point coil, an axial coil and a circumferential coil.

3. The method according to claim 1, wherein difference values between the characteristic amplitude values of the different two coils are related to the positions in the length of a crack.

4. The method according to claim 3, wherein at least one of the two different coils is a pancake coil.

5. The method according to claim 1, wherein the method is carried out using a computer program.

* * * * *